(12) United States Patent
Maiya

(10) Patent No.: US 8,022,373 B2
(45) Date of Patent: Sep. 20, 2011

(54) OBSERVING APPARATUS

(75) Inventor: Nobuhiko Maiya, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/329,756

(22) Filed: Dec. 8, 2008

(65) Prior Publication Data

US 2009/0159814 A1    Jun. 25, 2009

Related U.S. Application Data

(63) Continuation of application No. PCT/JP2007/061665, filed on Jun. 8, 2007.

(30) Foreign Application Priority Data

Jun. 8, 2006 (JP) .................................. 2006-159271

(51) Int. Cl.
*G01N 21/64* (2006.01)
(52) U.S. Cl. ...................................................... 250/461.2
(58) Field of Classification Search .................. None
See application file for complete search history.

(56) References Cited

U.S. PATENT DOCUMENTS

| | | | |
|---|---|---|---|
| 5,790,710 A | 8/1998 | Price et al. | |
| 2003/0103662 A1 | 6/2003 | Finkbeiner | |
| 2003/0210262 A1 | 11/2003 | Gahm et al. | |
| 2005/0058330 A1 | 3/2005 | Mitsuhashi et al. | |
| 2007/0031043 A1 * | 2/2007 | Perz et al. | 382/225 |

FOREIGN PATENT DOCUMENTS

| | | |
|---|---|---|
| EP | 0 510 329 A2 | 10/1992 |
| JP | 2000-292422 A | 10/2000 |
| JP | 2003-185936 A | 7/2003 |
| JP | 2005-117640 A | 4/2005 |
| JP | 2006-039171 A | 2/2006 |

OTHER PUBLICATIONS

"Understanding Bio-Imaging" Sep. 2005, pp. 22-24 (Published by Yodosha).
Extended European Search Report (and Search Opinion) from corresponding European Appln. No. 07767085 .9 issued Jun. 21, 2011.

* cited by examiner

*Primary Examiner* — David Porta
*Assistant Examiner* — Carolyn Igyarto
(74) *Attorney, Agent, or Firm* — Miles & Stockbridge P.C.

(57) ABSTRACT

An observing apparatus includes: a photographic unit that takes a region where cells are present as an observation object region based upon a macro image captured at low magnification of an interior of a cell culture vessel, and photographs the cells in the observation object region; an illuminating unit that irradiates light upon the cells only during photography by the photographic unit; and an output unit that outputs a fluorescent image photographed by the photographic unit while irradiating light only during photography by the illuminating unit. A recognition section recognizes at least one observation object region, within the macro image, in which cells are present. A selection unit selects a tiling mode or a random mode. A controller points an objective lens at an observation object region in which the recognition unit has recognized that cells are present.

5 Claims, 9 Drawing Sheets

OBSERVING APPARATUS

This application is a continuation of International Application No. PCT/JP2007/061665 filed Jun. 8, 2007.

INCORPORATION BY REFERENCE

The disclosures of the following priority application and the International Application are herein incorporated by reference: Japanese Patent Application No. 2006-159271 filed Jun. 8, 2006; and International Application No. PCT/JP2007/061665 filed Jun. 8, 2007.

BACKGROUND OF THE INVENTION

1. Field of the Invention

The present invention relates to an observing apparatus for observing an observation subject, and to an observing method.

2. Description of Related Art

The following type of method of observing cells by a fluorescence technique using a fluorescence microscope is known from Non-Patent Document #1. According to this method, excitation light is irradiated upon the cells, and the fluorescence emitted from the cells is observed. And, although setting of the observation position is performed before the observation, at this time, the excitation light is irradiated upon the cells, and setting of the observation position is performed from the fluorescent image.

Non-Patent Document #1: "Understanding Bio-Imaging", September 2005, pp. 22-24 (published by Yodosha).

SUMMARY OF THE INVENTION

However, with this prior art observing method, as the time period over which the excitation light is irradiated upon the cells becomes longer, the fluorescence becomes weaker due to photobleaching, and damage may be caused to the cells due to phototoxicity. Due to this there is a possibility that, when selecting one or more cells that are to be the subject of observation and setting the observation position, since a certain time is required for the task of selecting the cell, accordingly a bad influence may be undesirably exerted upon the cell at this selection stage due to photobleaching or phototoxicity, so that, during the actual observation, it becomes impossible to perform accurate observation.

According to the 1st aspect of the present invention, an observing apparatus comprises: a photographic unit that photographs cells based upon a macro image of an interior of a cell culture vessel in which the cells are put; an illuminating unit that irradiates light only during photography by the photographic unit; and an output unit that outputs a fluorescent image photographed by the photographic unit while irradiating light only during photography by the illuminating unit.

According to the 2nd aspect of the present invention, in the observing apparatus according to the 1st aspect, it is preferred that the photographic unit takes a region where the cells are present as an observation object region, and photographs the observation object region.

According to the 3rd aspect of the present invention, in the observing apparatus according to the 1st aspect, it is preferred that the illuminating unit irradiates light only upon a region where the cells are present.

According to the 4th aspect of the present invention, in the observing apparatus according to the 1st aspect, it is preferred that: the photographic unit takes a region where the cells are present as an observation object region, and photographs the observation object region; and the illuminating unit irradiates light only upon the region where the cells are present.

According to the 5th aspect of the present invention, in the observing apparatus according to the 1st aspect, it is preferred that the macro image is a tiling image formed by that each of small regions within the cell culture vessel is photographed repeatedly, and adjacent images of the small regions are joined together.

According to the 6th aspect of the present invention, in the observing apparatus according to the 1st aspect, it is preferred that: the observing apparatus further comprises a storage unit that stores the macro image; and specifying a cell in an observation object region is performed based upon the macro image stored in the storage unit.

According to the 7th aspect of the present invention, in the observing apparatus according to the 1st aspect, it is preferred that the observing apparatus further comprises a storage unit that stores the fluorescent image photographed by the photographic unit.

According to the 8th aspect of the present invention, in the observing apparatus according to the 1st aspect, it is preferred that the observing apparatus further comprises a recognition section that recognizes at least one region, within the macro image that has been acquired, in which cells are present.

According to the 9th aspect of the present invention, in the observing apparatus according to the 1st aspect, it is preferred that a magnification when imaging cells in the observation object region by the photographic unit is higher than a magnification when forming the macro image.

According to the 10th aspect of the present invention, in the observing apparatus according to the 8th aspect, it is preferred that the recognition section marks a region upon the macro image in which recognized cells are present.

According to the 11th aspect of the present invention, in the observing apparatus according to the 1st aspect, it is preferred that the photographic unit sets at least a region from among a plurality of regions in which the cells are present as an observation object region, selects at least a small region at random from within each observation object region that has been set, and performs photography of the small region that has been selected.

According to the 12th aspect of the present invention, in the observing apparatus according to the 1st aspect, it is preferred that the macro image is an image that has been observed by phase contrast observation, bright field observation, differential interference contrast observation, polarized light observation, or dark-field observation.

According to the 13th aspect of the present invention, in the observing apparatus according to the 8th aspect, it is preferred that the observing apparatus further comprises: an objective lens; a selection unit that selects a tiling mode or a random mode; and a controller that, when either the tiling mode or the random mode is selected, points the objective lens at a region in which it has been recognized by the recognition unit that the cells are present.

According to the 14th aspect of the present invention, in the observing apparatus according to the 13th aspect, it is preferred that: the observing apparatus further comprises an excitation light source that, during fluorescent observation, irradiates excitation light that excites a fluorescent reagent added to a specimen, and a shutter that can either intercept or allow irradiation of light from the excitation light source upon the specimen; and the controller controls the shutter so as to intercept the irradiation of light from the excitation light source upon the specimen, when the objective lens is facing to an observation position.

According to the 15th aspect of the present invention, in the observing apparatus according to the 14th aspect, it is preferred that the controller acquires a macro image of the observation region by, after having intercepted the excitation light with the shutter, performing observation by phase contrast observation, bright field observation, differential interference contrast observation, polarized light observation, or darkfield observation.

According to the 16th aspect of the present invention, in the observing apparatus according to the 15th aspect, it is preferred that after the macro image of the observation region has been acquired, the controller opens the shutter, irradiates excitation light from the excitation light source upon the specimen, and acquires a fluorescent image of the observation region.

According to the 17th aspect of the present invention, in the observing apparatus according to the 16th aspect, it is preferred that: the observing apparatus further comprises a storage unit that stores the fluorescent image that has been acquired; and the controller superimposes the fluorescent image of the observation region and the macro image of the observation region that are stored in the storage unit.

According to the 18th aspect of the present invention, in the observing apparatus according to the 1st aspect, it is preferred that the observing apparatus further comprises: a chamber in which a specimen can beset; a humidity regulator that adjusts a humidity within the chamber; and a temperature regulator that adjusts a temperature within the chamber.

According to the 19th aspect of the present invention, in the observing apparatus according to the 18th aspect, it is preferred that for a specimen set in an environment interior to the chamber that is regulated by the humidity regulator and the temperature regulator, acquisition of the macro image, irradiation upon the specimen by the illuminating unit, and acquisition of a fluorescent image by the photographic unit are performed.

According to the 20th aspect of the present invention, in the observing apparatus according to the 10th aspect, it is preferred that: the observing apparatus further comprises a display device that displays the macro image; and a mark is made upon the macro image that is displayed upon the display device.

DESCRIPTION OF PREFERRED EMBODIMENTS

Figure 1:
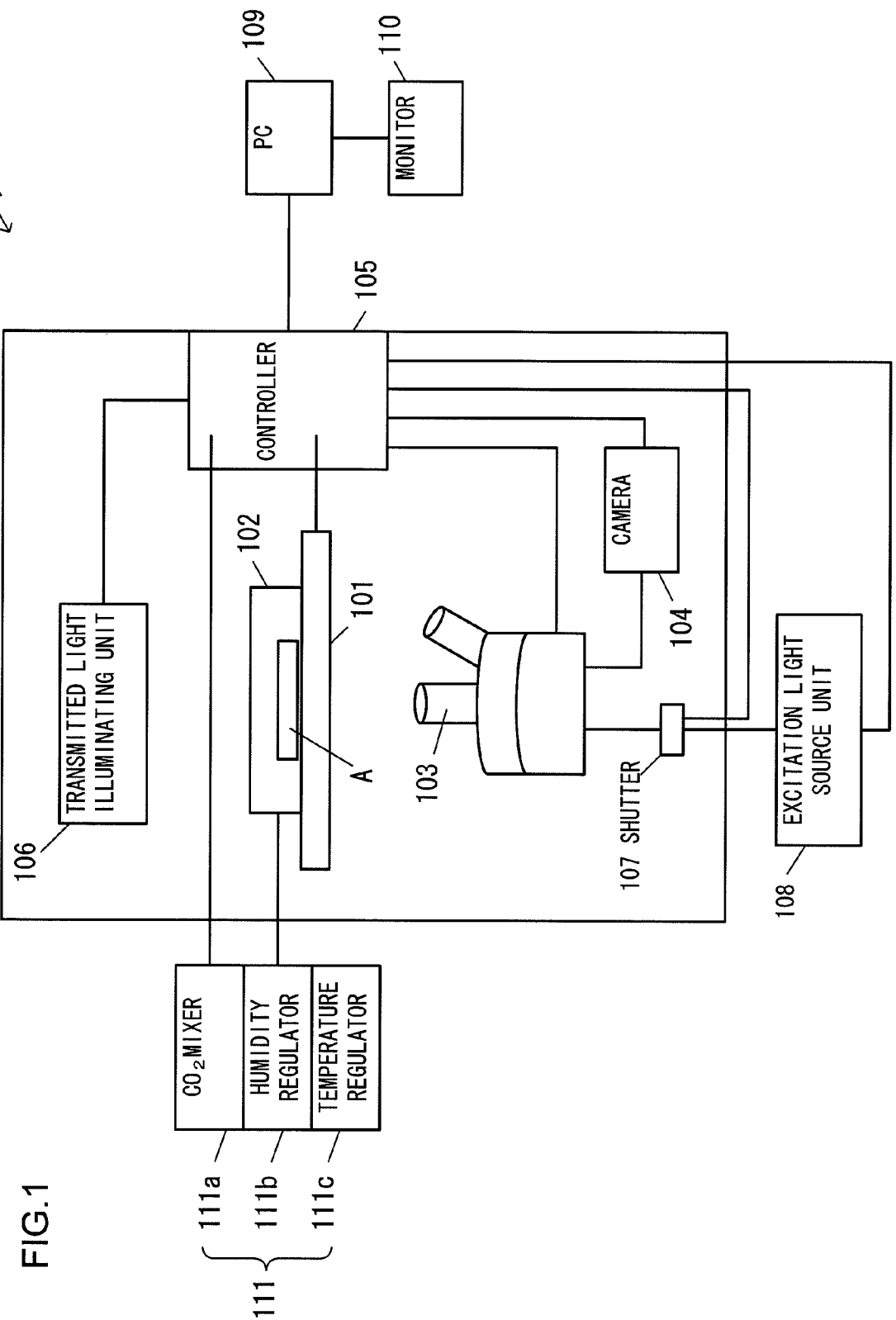
FIG. 1 is a figure schematically showing the structure of a cell observing apparatus.

FIG. 1 is a figure schematically showing the structure of the cell observing apparatus of this embodiment. This cell observing apparatus 100 includes a stage 101, a chamber 102, an objective lens 103, a camera 104, a controller 105, a transmitted light illuminating unit 106, a shutter 107, an excitation light source unit 108, a personal computer (PC) 109, a monitor 110, and an environment controller 111. It should be understood that the stage 101, the chamber 102, the objective lens 103, the camera 104, the controller 105, the transmitted light illuminating unit 106, the shutter 107, and the excitation light source unit 108 constitute a microscope.

With this cell observing apparatus 100, various commands can be sent to the cell observing apparatus 100 by the user actuating the PC 109, and the PC 109 outputs control signals to a controller 105 according to these commands from the user. And, on the basis of the control signals from the PC 109, the controller 105 performs various types of processing according to the commands from the user. In this embodiment, processing when observing cells within a cell culture vessel A that has been set by the user upon the stage 101 within the chamber 102 will be explained.

It should be understood that, for the cell culture vessel A, for example, a 35 mm dish may be used. Moreover, the interior of the chamber 102 is sealed, and its internal environment is maintained by the environment controller 111 at an environment that is suitable for culturing cells. For example, the $CO_2$ density within the chamber 102 may be maintained at 5% by a $CO_2$ mixer 111a, the humidity may be maintained at 100% by a humidity regulator 111b, and the temperature may be maintained at 37° C. by a temperature regulator 111c.

The excitation light source unit 108 irradiates the cell culture vessel A within the chamber 102 with excitation light of a wavelength that excites a fluorescent pigment with which the cells are dyed. It should be understood that it is possible to intercept this excitation light that is outputted from the excitation light source unit 108 with the shutter 107. The transmitted light illuminating unit 106 includes a LED that functions as a light source, and the LED may be caused to emit light when the excitation light is intercepted by the shutter 107, so that it is also possible to irradiate transmitted light (illumination light) upon the cell culture vessel A within the chamber 102. The interception of excitation light by the shutter 107 and the emission of LED light from the transmitted light illuminating unit 106 are both controlled by the controller 105.

The microscope has a phase contrast observation mode and a fluorescent observation mode: it can perform phase contrast observation of the cells by irradiating transmitted light upon the cell culture vessel A within the chamber 102, and also it can irradiate excitation light from the excitation light source unit 108 upon the cell culture vessel within the chamber 102, thus performing fluorescent observation of the cells that have been dyed with a fluorescent reagent. The camera 104 includes an image sensor such as a CCD or the like, and is able to obtain a microscopic image by capturing an image (a magnified image) of the cells that is inputted via the objective lens 103, in other words is able to capture both a phase contrast image and a fluorescent image. Furthermore, this microscope can be used either with an objective lens of high magnification for observing the cells, or with an objective lens of low magnification that can observe a wide field of view of 4× or the like, by changing them over.

It should be understood that this microscope may perform fluorescent observation via a plurality of fluorescent filters that can be changed over. For example, if multiple dyeing has been performed by dyeing with a plurality of fluorescent reagents, then it is possible to observe a plurality of fluorescent colors by performing fluorescent observation while changing over the plurality of fluorescent filters. By doing this, the camera 104 can capture a plurality of fluorescent images with a plurality of fluorescent filters respectively.

The microscopic image that has been photographed by the camera 104 is outputted to the controller 105, and is then displayed upon the monitor 110 after having been outputted to the PC 109. Due to this, the user is able to check the microscopic image upon the monitor 110.

With the cell observing apparatus 100 of this embodiment, by actuating the PC 109, the user is able to command the photographic conditions for the fluorescent image according to the type of the cells that are the subject of observation. For example the user may command, as photographic conditions, the amount of excitation light, the camera gain, the exposure time, the focal plane, and the filter type. These photographic conditions are set for each type of cells in advance and are stored within a memory provided to the PC 109, and the user may either select from these set contents according to the type of the cells that are the subject of observation, or may set the photographic conditions each time he performs observation.

Generally, when performing fluorescent observation of cells, as the time period over which the excitation light is irradiated upon the cells becomes longer, the fluorescence becomes weaker due to photobleaching, and damage may be caused to the cells due to phototoxicity. Due to this the possibility arises that if, before performing the actual fluorescent observation (the main fluorescent observation), as a preliminary step, a fluorescent observation (a preparatory fluorescent observation) is performed in order to choose one or more cells as the subject for observation, then, since a certain period of time is required for this preparatory fluorescent observation, a bad influence may be exerted upon the cell or cells at this preparatory fluorescent observation stage due to photobleaching or phototoxicity, which is undesirable because subsequently it may become impossible to obtain accurate experimental data and so on during the main fluorescent observation, so that it may become impossible to obtain the anticipated observational results.

The method will now be explained according to which, in this embodiment, in order to keep the bad influence exerted upon the cells at the preparatory observation stage to a minimum limit, the time period over which the excitation light is irradiated at the preparatory observation stage is kept to the minimum possible limit.

First, using an objective lens that can perform observation over a wide field of view such as 4× or the like, by performing phase contrast observation of the entire range within the observable region while shifting the objective lens, the controller 105 photographs a phase contrast image. "Within the observable region" here means within the interior of the cell culture vessel A. And a single image is built up by joining together (i.e. by tiling) a plurality of images that have been photographed while thus shifting the objective lens. In the following, the image that is thus built up will be termed the "macro image". After building up the macro image, the controller 105 outputs it to the PC 109.

A CPU that is incorporated in the PC 109 analyzes the macro image that has been inputted using an image analysis technique such as per se known texture analysis or the like, and recognizes the regions within the macro image where the cells are growing (i.e. the cell growth regions). And the CPU picks out (i.e. marks) the cell growth regions that have been recognized upon the macro image, and displays them on the monitor 110. Due to this, the user (i.e. the experimenter) is able to confirm whether or not cell growth regions are present within the observable range, and in what positions.

Figure 2:
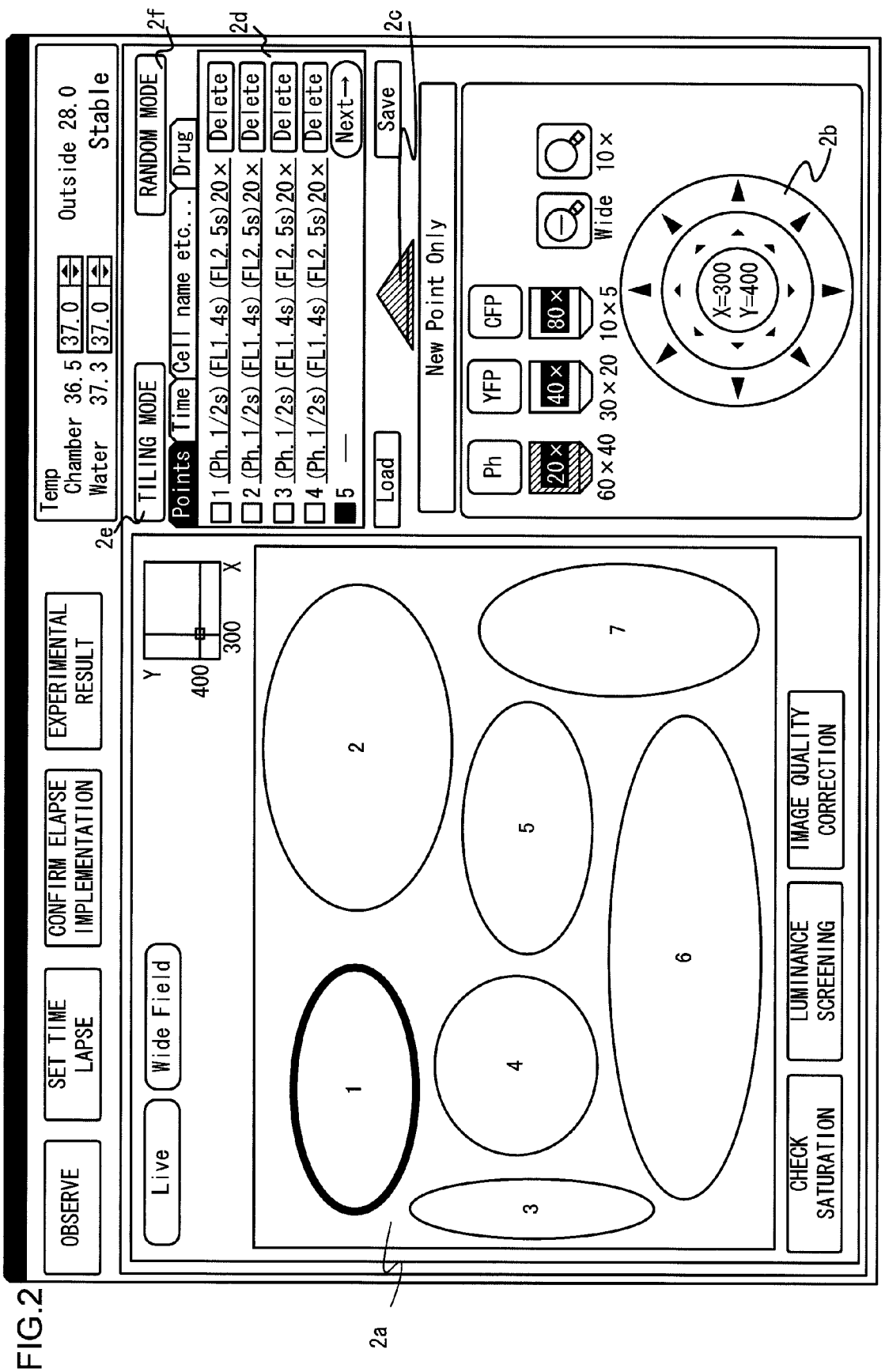
FIG. 2 is a figure showing a concrete example of a screen for confirmation of a growth region.

The CPU may, for example, display upon the monitor 110 a GUI screen (a screen for growth region checking) in which the macro image is displayed, as shown in FIG. 2. On this screen for growth region checking there is displayed, within a macro image display region 2a, a macro image in which cell growth regions 1 through 7 are picked out. And the user selects one or more regions from these cell growth regions 1 through 7 to be the subject of executing navigation that will be described hereinafter. "Executing navigation" means automatically acquiring a microscope image of the designated region or regions with a method set in advance, under photographic conditions determined in advance and so on. It should be understood that although, in FIG. 2, the cell growth regions are schematically shown as being circular or elliptical, actually the shapes of the regions in which the cells are growing are displayed.

In concrete terms, using a mouse provided to the PC 109, the user actuates a shift button 2b upon the screen for growth region checking, and changes the state of selection of the cell growth regions 1 through 7. For example, the cell growth region that is currently selected may be displayed with a thick frame (highlight display), and the state of selection of the cell growth regions 1 through 7 may be changed by shifting the thick frame according to the state of actuation of the shift button 2b. In the example shown in FIG. 2, it is supposed that the shift button 2b is a circular shaped button, and that the state of selection of the cell growth regions is changed according to the position upon the button that has been clicked with the mouse.

By the user clicking a select button 2c in the state in which that cell growth region that he desires to make the subject for execution of navigation is displayed with a thick frame, he selects the cell growth region to be the subject for execution of navigation. When a cell growth region is selected by the user, the CPU registers, in a selection information display region 2d, information that specifies the position of the cell growth region that has been selected within the macro image display region 2a. It should be understood that, if the user desires for a plurality of cell growth regions to be the subjects of execution of navigation, then he performs the processing described above repeatedly, and thereby registers information related to that plurality of cell growth regions in the selection information display region 2d.

Moreover, the user selects either the tiling mode or the random mode as the method for executing navigation processing for the cell growth regions that have been selected. In this embodiment, the user selects a navigation method by clicking the mouse upon either a tiling mode button 2e or a random mode button 2f on the screen for growth region checking, and then commands execution of navigation by the selected method. It should be understood that both these navigation methods, i.e. the tiling mode and the random mode, will be described hereinafter.

When this command for navigation execution is issued by the user, the CPU generates a recipe in which are stored items of information related to a range (i.e. a navigation range) or spots (i.e. navigation spots), for execution of navigation within the macro image display region 2a, to the method of navigation, and to the photographic conditions described above, according to the navigation method that has been selected, and outputs this recipe to the controller 105. And, upon input of this recipe from the PC 109, the controller 105 executes navigation as will be described hereinafter, on the basis of the various items of information that are stored in the recipe.

In the following, the case in which the navigation method that has been selected by the user is the tiling mode, and the case in which it is the random mode, will be considered separately, and the navigation method in each of these modes will be explained. It should be understood that although, in the following explanation, the case is explained in which a single cell growth region is selected as the navigation subject cell growth region (i.e. as the navigation subject region), nevertheless it would also be acceptable, if a plurality of navigation subject regions have been selected, to perform the processing explained below upon each of these navigation subject regions.

(1) When the Navigation Method is Tiling Mode

When the tiling mode button 2e is clicked by the user, and a command is issued for navigation to be executed according to the tiling mode, the CPU generates a recipe as described above, that sets the XY coordinate group around the periphery of the cell growth region that has been selected as the information specifying the navigation range (the navigation range information). By this recipe being outputted to the controller 105, execution of the navigation is commanded from the PC 109 to the controller 105. And, in response to this execution command for navigation from the PC 109, the controller 105 executes navigation to the navigation subject region, as will now be described.

First, the controller 105 reads in information, stored in the recipe, related to the navigation range information and to the photographic conditions. And, on the basis of the navigation range information, the controller 105 specifies the coordinate values (X,Y) of an initial starting point for the navigation range. For example, the controller 105 may specify the coordinate values of the upper left end point of the navigation range as being the coordinate values (X,Y) of the initial starting point of the navigation range.

And, after having set the microscope to the phase contrast observation mode, having shifted the objective lens 103 to the initial starting point of the navigation mode that has been specified, and having intercepted the excitation light by closing the shutter 107, the controller 105 controls the transmitted light illuminating unit 106 so as to cause the LED to emit light for just the time period that is required for photography of a phase contrast image, i.e., for example, for just the exposure time for the camera 104. And the objective lens 103 is set to high magnification, the camera 104 is controlled so as to perform photography of the image that is inputted via the objective lens 103 at this time, and this image is stored. Due to this, it is possible to photograph a phase contrast image at the initial starting point of the navigation range.

Furthermore, the controller 105 sets the microscope to the fluorescent observation mode, controls the transmitted light illuminating unit 106 so as to turn the LED off, and irradiates excitation light by opening the shutter 107 for just the time period that is required for photography of a fluorescent image, for example for just the exposure time of the camera 104. And the objective lens 103 is set to high magnification, the camera 104 is controlled so as to perform photography of the image that is inputted via the objective lens 103 at this time, and this image is stored. Due to this, it is possible to photograph a'fluorescent image at the initial starting point of the navigation range. It should be understood that, at this time, if the types of a plurality of fluorescent filters are set in the photographic conditions, then, by changing over these fluorescent filters, a fluorescent image is photographed for each of the fluorescent filters.

Thereafter, the controller 105 shifts the objective lens 103 so as to photograph the next region within the navigation range. In other words, the controller 105 controls the shift amount of the objective lens 103 so that the photographic range of the camera 104 with the objective lens at its position after shifting is adjacent to the photographic range of the camera 104 with the objective lens at its position before shifting, and moreover so that the two ranges do not overlap. And the above described processing is executed for the objective lens position after shifting, so that a phase contrast image and a fluorescent image at the objective lens position after shifting are photographed and stored. By performing this processing over the entire scope of the navigation range, for each of the small regions within the navigation range, it is possible to photograph a phase contrast image and a plurality of fluorescent images classified according to the types of filter.

And the controller 105 joins together (tiles together) the phase contrast images that correspond to the various small regions that have been photographed while performing navigation, and thereby builds up a single joined-up image (a macro phase contrast image) that has been photographed over the entire navigation range. Moreover, in a similar manner, for each of the fluorescent filters used for the fluorescent images, the controller 105 builds up a joined-up image (a macro fluorescent image) for that fluorescent filter by tiling together the fluorescent images for that filter that correspond to the various small regions.

Figure 3A:
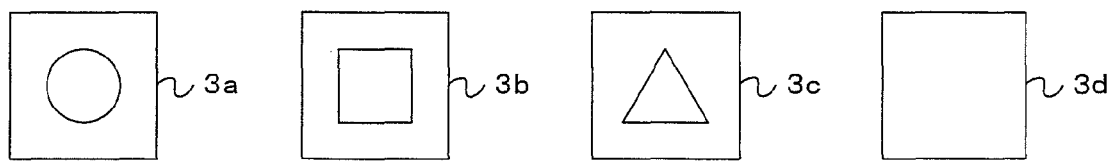
FIGS. 3A-3C are figures schematically showing steps for creating a macro phase contrast image.
Figure 3B:
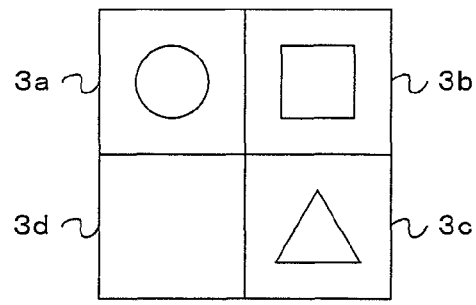
Figure 3C:
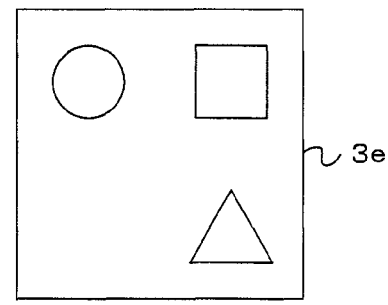

Now the method by which the macro phase contrast image is built up will be explained in concrete terms using FIGS. 3A-3C. These FIGS. 3A-3C are figures that schematically show the steps for building up a macro phase contrast image on the basis of phase contrast images that have been photographed while performing navigation to each of four small regions in turn. Here, the result of performing navigation to these four small regions as subjects is that the four phase contrast images 3a through 3d shown in FIG. 3A are photographed. The controller 105 performs the tiling by arranging these four phase contrast images as shown in FIG. 3B, i.e. while keeping their relative positional relationships just the same as those of the respectively corresponding small regions within the navigation range, and by then joining them together. By doing this, a macro phase contrast image 3e as shown in FIG. 3C is built up.

Figure 4A:
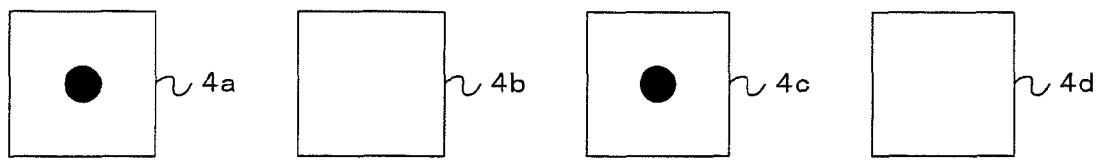
FIGS. 4A-4F are figures schematically showing steps for creating a macro fluorescent image.

Next, the method by which the macro fluorescent images are built up will be explained in concrete terms with reference to FIGS. 4A-4F. These FIGS. 4A-4F are figures that schematically show the steps for building up a macro fluorescent image on the basis of fluorescent images that have been photographed while performing navigation to each of four small regions in turn while using two different fluorescent filters. Here, the result of performing navigation to these four small regions as subjects using the first fluorescent filter is that the four fluorescent images 4a through 4d shown in FIG. 4A are photographed. Moreover, the result of performing navigation to these four small regions as subjects using the second fluorescent filter is that the four fluorescent images 4f through 4i shown in FIG. 4D are photographed.

Figure 4B:
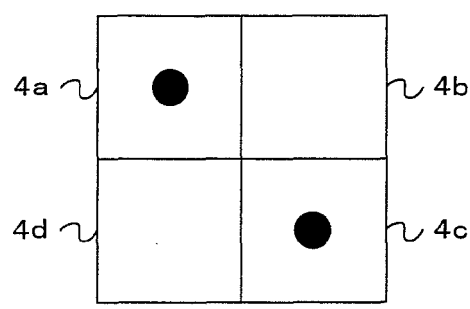
Figure 4C:
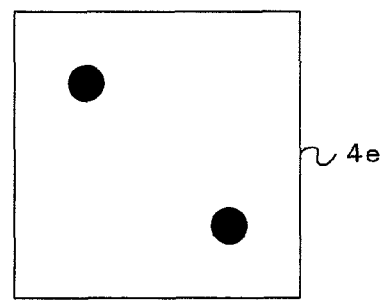
Figure 4D:
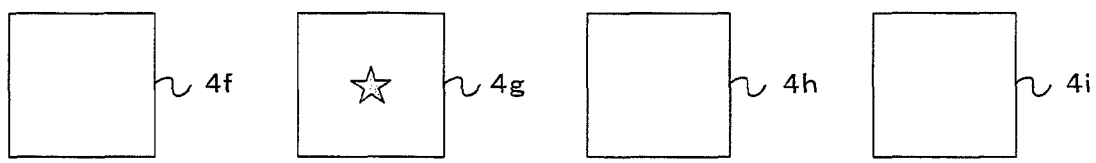
Figure 4E:
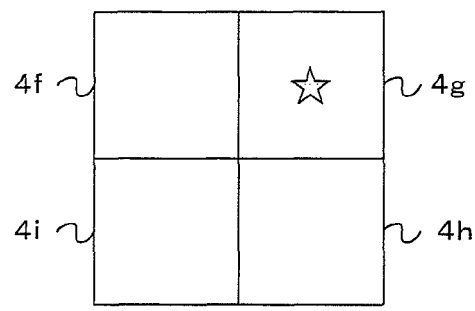
Figure 4F:
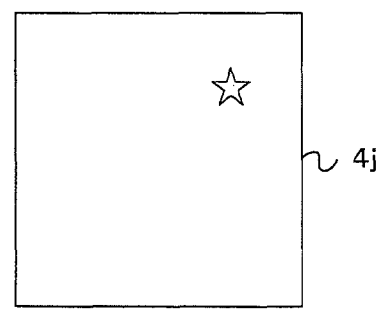

The controller 105 performs the tiling by, first, arranging the four fluorescent images 4a through 4d shown in FIG. 4A as shown in FIG. 4B, i.e. while keeping their relative positional relationships just the same as those of the respectively corresponding small regions within the navigation range, and by then joining them together. By doing this, a macro fluorescent image 4e for the first fluorescent filter is built up, as shown in FIG. 4C. Next, the controller 105 performs the tiling by arranging the four fluorescent images 4f through 4i shown in FIG. 4D as shown in FIG. 4E, i.e. while keeping their relative positional relationships just the same as those of the respectively corresponding small regions within the navigation range, and by then joining them together. By doing this, a macro fluorescent image 4j for the second fluorescent filter is built up, as shown in FIG. 4F.

The controller 105 outputs to the PC 109 the macro phase contrast image and the macro fluorescent images for each fluorescent filter that have been built up in this manner.

(2) When the Navigation Method is Random Mode

When the random mode button 2*f* is clicked by the user, and a command is issued for navigation to be executed according to the random mode, the CPU invites the user to input the number of spots that are to be set as navigation spots. When in response to this command the user actuates the keyboard provided to the PC 109 and inputs a number of spots equal to one or more, then the CPU selects at random, within the navigation subject region, spots to the number inputted by the user.

And the CPU generates a recipe that sets the XY coordinate values of the spots that have been randomly selected within the navigation subject region as information specifying the navigation spots (the navigation spot information). By this recipe being outputted to the controller 105, execution of the navigation is commanded from the PC 109 to the controller 105. And, in response to this execution command for navigation from the PC 109, the controller 105 executes navigation to the navigation subject region, as will now be described.

First, the controller 105 reads in information, stored in the recipe, related to the navigation spot information and to the photographic conditions. And, on the basis of the navigation spot information, the controller 105 specifies the coordinate values (X,Y) of the various navigation spots. Moreover, after having set the microscope to the phase contrast observation mode, having shifted the objective lens 103 to any one of the spots among the navigation spots that have been specified, and having intercepted the excitation light by closing the shutter 107, the controller 105 controls the transmitted light illuminating unit 106 so as to cause the LED to emit light for just the time period that is required for photography of a phase contrast image, i.e., for example, for just the exposure time for the camera 104. And the objective lens 103 is set to high magnification, and the camera 104 is controlled so as to perform photography of the image that is inputted via the objective lens 103 at this time. Due to this, it is possible to photograph a phase contrast image of a small region centered around the navigation spot.

Furthermore, the controller 105 sets the microscope to the fluorescent observation mode, controls the transmitted light illuminating unit 106 so as to turn the LED off, and irradiates excitation light by opening the shutter 107 for just the time period that is required for photography of a fluorescent image, for example for just the exposure time of the camera 104. And the objective lens 103 is set to high magnification, and the camera 104 is controlled so as to perform photography of the image that is inputted via the objective lens 103 at this time. Due to this, it is possible to photograph a fluorescent image of the small region centered around the navigation spot. It should be understood that, at this time, if the types of a plurality of fluorescent filters are set in the photographic conditions, then, by changing over these fluorescent filters, a fluorescent image is photographed for each of the fluorescent filters.

Thereafter, the controller 105 shifts the objective lens 103 to a navigation spot for which photography of an image has not yet been performed. And the above described processing is executed for the objective lens position after shifting, so that a phase contrast image and a fluorescent image of the small region centered around this navigation spot are photographed and stored. By performing this processing for all of the navigation spots that are stored in the recipe, it is possible to photograph, for each of the small regions centered around the navigation spots that have been selected at random from within the navigation subject region, a phase contrast image (a spot phase contrast image) and a plurality of fluorescent images (spot fluorescent images) classified according to the types of filter.

For example, if four points have been designated as navigation spots, then the four phase contrast images 3*a* through 3*d* shown in FIG. 3A may be photographed, and, in a similar manner, the four fluorescent images 4*a* through 4*d* shown in FIG. 4A and the four fluorescent images 4*f* through 4*i* shown in FIG. 4D may be photographed. And the controller 105 outputs to the PC 109, for each navigation spot, the spot phase contrast images and the spot fluorescent images for each fluorescent filter that have been photographed in this manner.

Figure 5:
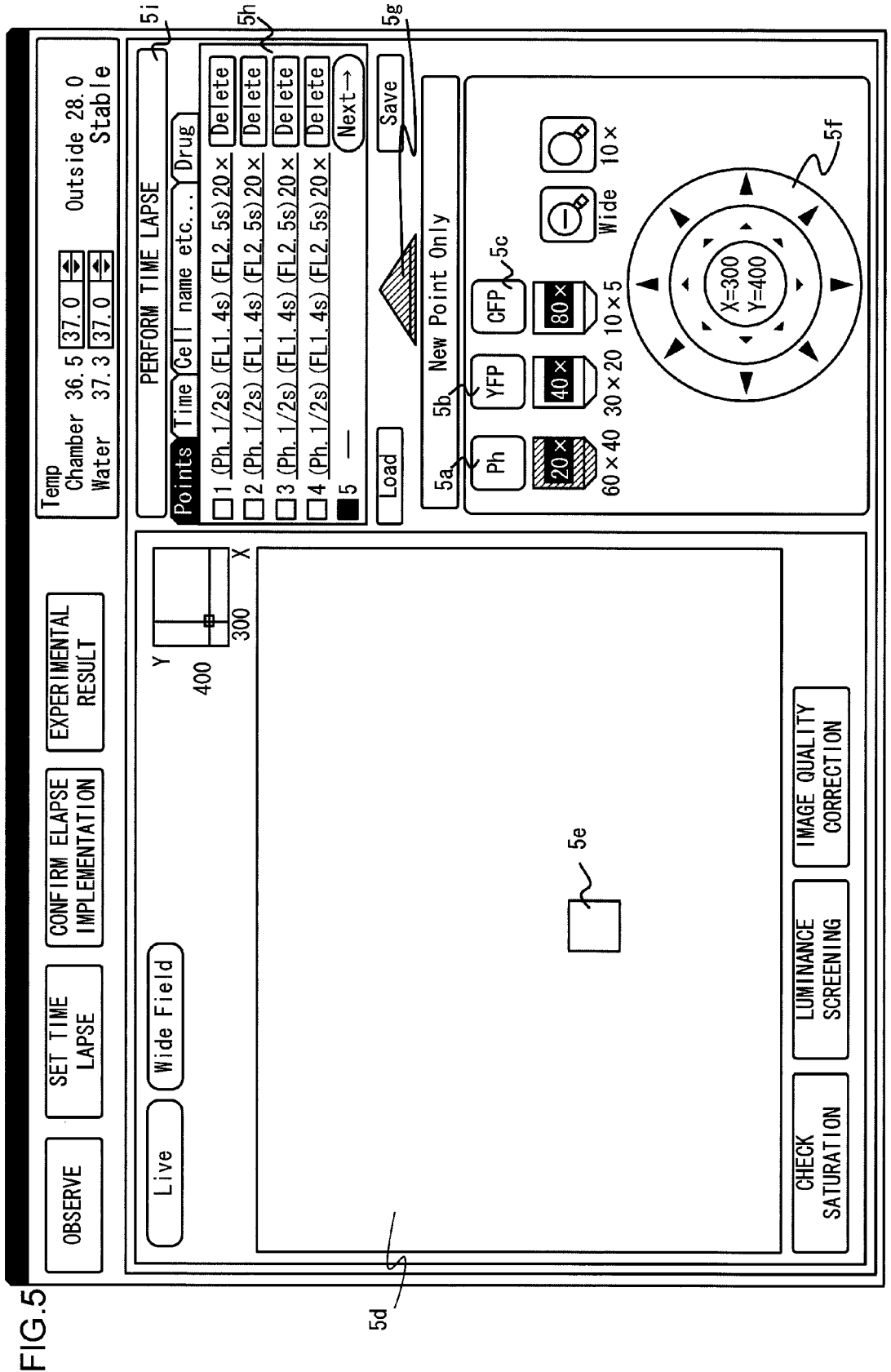
FIG. 5 is a figure showing a concrete example of a screen for observation subject selection.

The CPU in the PC 109 displays on the monitor 110 a GUI screen (a screen for observation subject selection) as for example shown in FIG. 5. By actuating this screen for observation subject selection upon the monitor 110, on the basis of the images that are inputted from the controller 105 corresponding to each observation method, the user selects a cell that is to be the subject for observation in the following manner. It should be understood that the user actuates the screen for observation subject selection shown in FIG. 5 by actuating the mouse that is provided to the PC 109. Moreover, with regard to the screen for observation subject selection shown in FIG. 5, only items related to this embodiment will be explained, while explanation with regard to other items will be omitted.

In the following explanation, the processing will be explained in detail for the case in which the tiling mode is selected as the navigation mode, when the above described macro phase contrast image and the macro fluorescent images for each of the fluorescent filters have been inputted. With regard to the case of the processing when the random mode has been selected as the navigation mode, processing may be performed in a similar manner to that described below by performing similar processing with, in the following explanation, the macro phase contrast image being replaced by the spot phase contrast image, and the macro fluorescent images being replaced by the corresponding spot fluorescent images. At this time the user needs to perform actuation for each of the images by changing over to the spot images for each of the navigation spots, since, by contrast to the fact that, in a navigation range over which tiling has been performed, the macro image is a single image, with spot images, there are spot images for each of the plurality of small regions that correspond to the navigation spots.

First, the user selects a phase contrast image display button 5*a* upon the screen for observation subject selection, and displays the macro phase contrast image within the image display region 5*d* upon the screen for observation subject selection. And the user is able to check the shapes of the cells with this macro phase contrast image. And, with this macro phase contrast image as a base, he is able to display, superimposed thereupon, the macro fluorescent image (the filter image) that has been photographed with any desired fluorescent filter. For example, when the user wishes to display the filter image that has been obtained during fluorescent observation by photographing an image while emitting red colored light as superimposed upon the macro phase contrast image, then he selects a red color filter image display button 5*b* upon the screen for observation subject selection. In other words, by establishing a state in which both the phase contrast image display button 5*a* and the red color filter image display button 5*b* have been selected, the user is able to display, within the image display region 5*d*, the red color filter image as superimposed upon the macro phase contrast image as a base.

In a similar manner, if the user wishes to display the filter image that has been obtained during fluorescent observation by photographing an image while emitting blue colored light as superimposed upon the macro phase contrast image, then he selects both the phase contrast image display button 5a and also a blue color filter image display button 5c upon the screen for observation subject selection. Moreover, if he wishes to display both the red color filter image and also the blue color filter image as superimposed upon the macro phase contrast image, then he selects all of the phase contrast image display button 5a, the red color filter image display button 5b, and the blue color filter image display button 5c.

Figure 6:
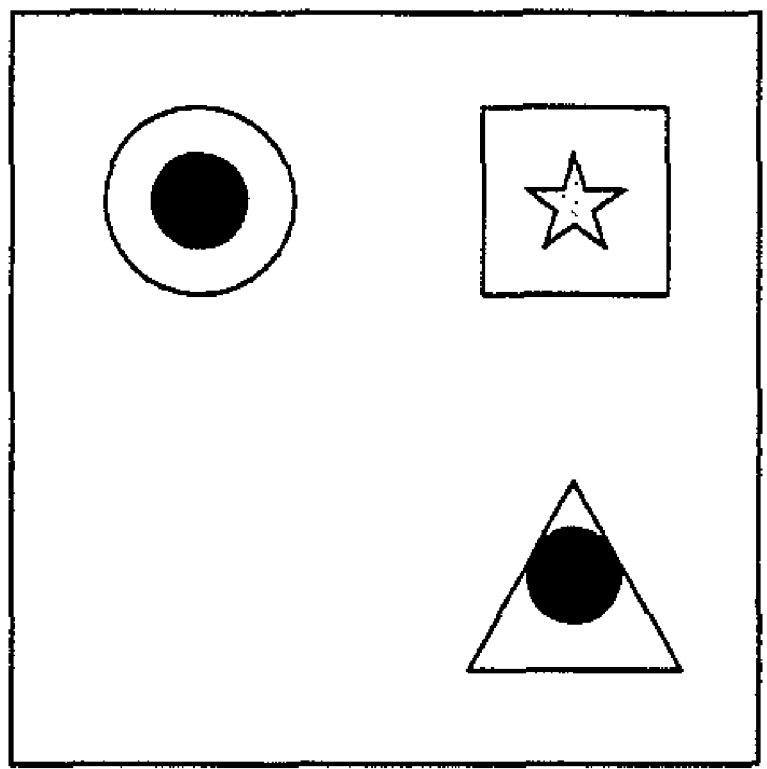
FIG. 6 is a figure showing a concrete example of a case in which a macro phase contrast image and a macro fluorescent image are superimposed.

For example, when displaying the first fluorescent filter image 4e and the second filter image 4j shown in FIGS. 4C and 4F as superimposed upon the macro phase contrast image 3e shown in FIG. 3C, then a combined image as shown in FIG. 6 is displayed within the image display region 6d.

By providing a display in which the combined macro phase contrast images and the combined macro fluorescent images (i.e. the filter images) are superimposed in this manner, the user is enabled, while checking the shapes of the cells and the state of fluorescence of the fluorescent reagent, also to perform selection of the cell(s) to be the subject(s) for the main observation. In concrete terms, after having shifted the cursor 5e that is displayed over the macro image within the image display region 5d by actuating a shift button 5f with the mouse, the user selects a cell to be the subject for the main observation by clicking a select button 5g with the mouse. And, if the user wishes to select a plurality of cells to be the observation subjects for the main observation, then he repeats this process.

It should be understood that the shift button 5f is a circular shaped button on this screen for observation subject selection as well, just as was the case with the screen for navigation position designation described above in connection with FIG. 2. And the direction of shifting of the cursor 5e upon the screen is determined according to the position upon this button that is clicked with the mouse, and the shift amount of the cursor 5e upon the screen is determined according to the number of times depression by the mouse is performed, or according to the time period of depression.

When a cell that is to be the subject of observation during the main observation is selected by the user, the CPU attaches information within this observation subject display region 5h that specifies the position of the cursor 5e at the time point that the select button 5g was clicked.

Due to this, the user is able to select a cell that is to be the subject of observation at the preparatory stage before the actual main observation, i.e. while looking at the macro image that has been displayed upon the monitor 110, and it is possible to manage without continuously irradiating transmitted light or excitation light upon the cells for selecting a cell. In other words, since it is possible to manage with the irradiation time period for the excitation light being only that time period that is required for photography of the fluorescent images, accordingly it is possible to reduce the damage to the cells at this preparatory stage due to photobleaching or phototoxicity to the minimum possible level. Moreover, since it is possible to manage with the irradiation time period for the transmitted light being only that time period that is required for photography of the phase contrast image, accordingly, even if a bad influence is exerted upon the cells due to the transmitted light, it is possible to reduce this bad influence to the minimum possible level.

When thereafter, by actuating the PC 109, the user issues a command to start the main observation, the CPU outputs to the controller 105 the information displayed in the main observation subject display region 5h and also a command signal for execution of the main observation. For example, the user may command starting of the main observation for the cells that are displayed within the main observation subject display region 5h as having been selected, by clicking a time lapse execute button 5i shown in FIG. 5. It would also be acceptable to arrange, when acquiring the image that has been observed during this main observation, to shift the photographic position one small region at a time within the region that has been selected, for the selected cell (s), and to tile the images that have thus been photographed.

When this execute command signal for the main observation is inputted, the controller 105 performs a cell observation by observing the cell(s) that are to be the subject(s) for observation by, for example, executing time lapse processing; in other words, the controller 105 performs the main observation. The result of this main observation is outputted to the PC 109 via the controller 105, and the observation data (the test data) are recorded upon the hard disk within the PC 109 and are simultaneously displayed upon the monitor 110.

Figure 7:
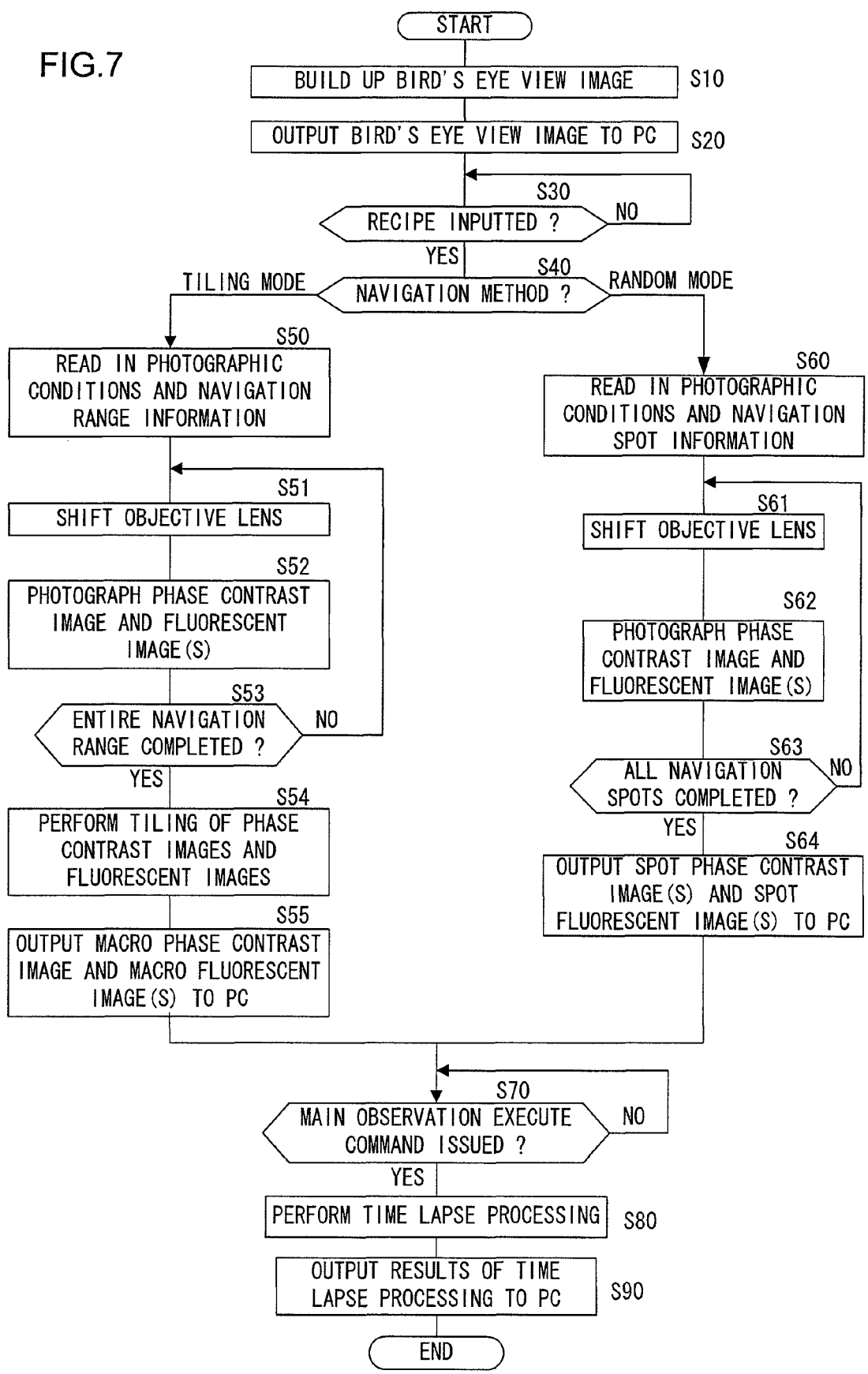
FIG. 7 is a flow chart showing the flow of processing of a controller 105.

FIG. 7 is a flow chart showing the flow of processing of the controller 105. The processing shown in FIG. 7 is executed by the controller 105 as a program that starts when the starting of preparations for testing is commanded by the PC 109 being actuated by the user, upon which a testing start signal is received from the PC 109.

In a step S10 the microscope is set to the phase contrast observation mode, and, while using an objective lens of low magnification that can perform observation over a wide field of view such as 4× or the like, phase contrast images of the entire range within the region that can be observed are photographed while shifting the objective lens, so that the macro image described above is built up by joining together the plurality of images that are thus photographed. Thereafter the flow of control proceeds to a step S20 in which the macro image that has been built up is outputted to the PC 109, and then the flow of control proceeds to a step S30.

In the step S30, a decision is made as to whether or not a recipe as described above has been inputted from the PC 109. If it is decided that a recipe has been inputted, then the flow of control proceeds to a step S40. In this step S40, on the basis of navigation method information that is stored in the recipe, a decision is made as to whether the navigation method that has been selected by the user upon the PC 109 is the tiling mode or the random mode. If it is decided that the navigation method is the tiling mode, then the flow of control proceeds to a step S50.

In the step S50 information, stored in the recipe, is read in relating to the navigation range information and the photographic conditions, and then the flow of control proceeds to a step S51. In this step S51, the coordinate values (X,Y) of the initial starting point of the navigation range are specified on the basis of the navigation range information, and the objective lens 103 is shifted to this initial starting point of the navigation range that has been specified.

Then the flow of control proceeds to a step S52, in which navigation is performed as described above by controlling the objective lens 103, the camera 104, the transmitted light illuminating unit 106, and the shutter 107, while changing the microscope over between the phase contrast observation mode or the fluorescent observation mode, so that a phase contrast image and a fluorescent image are photographed for each small region. At this time, if the types of a plurality of fluorescent filters are set in the photographic conditions, then, by changing over the plurality of fluorescent filters, a fluorescent image is photographed for each type of filter. Then the flow of control proceeds to a step S53.

In this step S53, a decision is made as to whether or not navigation has been completed over the entire navigation range. If it is decided that the execution of the navigation has not been completed, then the flow of control returns to the step S51, the objective lens 103 is shifted in order to photograph an adjacent small region, and the above processing is repeated. By contrast, if it is decided that the execution of the navigation has been completed, then the flow of control proceeds to a step S54.

In this step S54, the phase contrast images for each small region that have been photographed while executing navigation, and the fluorescent images of at least one type that have also been photographed, are tiled together, and thus the above described macro phase contrast image and macro fluorescent image or images are created. Then the flow of control proceeds to a step S55, in which the macro phase contrast image and macro fluorescent image(s) that have been created are outputted to the PC 109, and then the flow of control is transferred to a step S70 that will be described hereinafter.

By contrast, if it is decided that the navigation mode that has been selected by the user on the PC 109 is the random mode, then the flow of control is transferred to a step S60. In this step S60 information stored in the recipe relating to the photographic conditions and to the navigation spots is read in, and then the flow of control proceeds to a step S61. In this step S61 the coordinate values of the navigation spots are specified, and then the objective lens is shifted to one among these navigation spots that have thus been specified.

Then the flow of control proceeds to a step S62 in which, by controlling the objective lens 103, the camera 104, the transmitted light illuminating unit 106, and the shutter 107 as described above, a phase contrast image and a fluorescent image are photographed for a small region that is centered upon the navigation spot. At this time, if the types of a plurality of fluorescent filters are set in the photographic conditions, then, by changing over the plurality of fluorescent filters, a fluorescent image is photographed for each type of filter. Then the flow of control proceeds to a step S63.

In this step S63, a decision is made as to whether or not photography of a phase contrast image and of fluorescent image(s) has been completed for all of the navigation spots. If it is decided that this photography has not been completed, then the flow of control returns to the step S61, the objective lens 103 is shifted to a navigation spot for which photography of the above images has not been performed, and the above processing is repeated. By contrast, if it is decided that the execution of the navigation has been completed, then the flow of control proceeds to a step S64. In this step S64, the spot phase contrast images of the small regions that correspond to each of the navigation spots, and the spot fluorescent images thereof for each of the fluorescent filters, are outputted to the PC 109, and then the flow of control proceeds to a step S70.

In this step S70, a decision is made as to whether or not a command signal for execution of the main observation has been received from the PC 109. If it is decided that a command signal for execution of the main observation has been received, then the flow of control proceeds to a step S80, in which time lapse processing is executed upon the cell(s) that have been selected by the user upon the PC 109 to be the subject of observation. Then the flow of control proceeds to a step S90, in which the result of this time lapse processing is outputted to the PC 109, and then this processing terminates.

Figure 8:
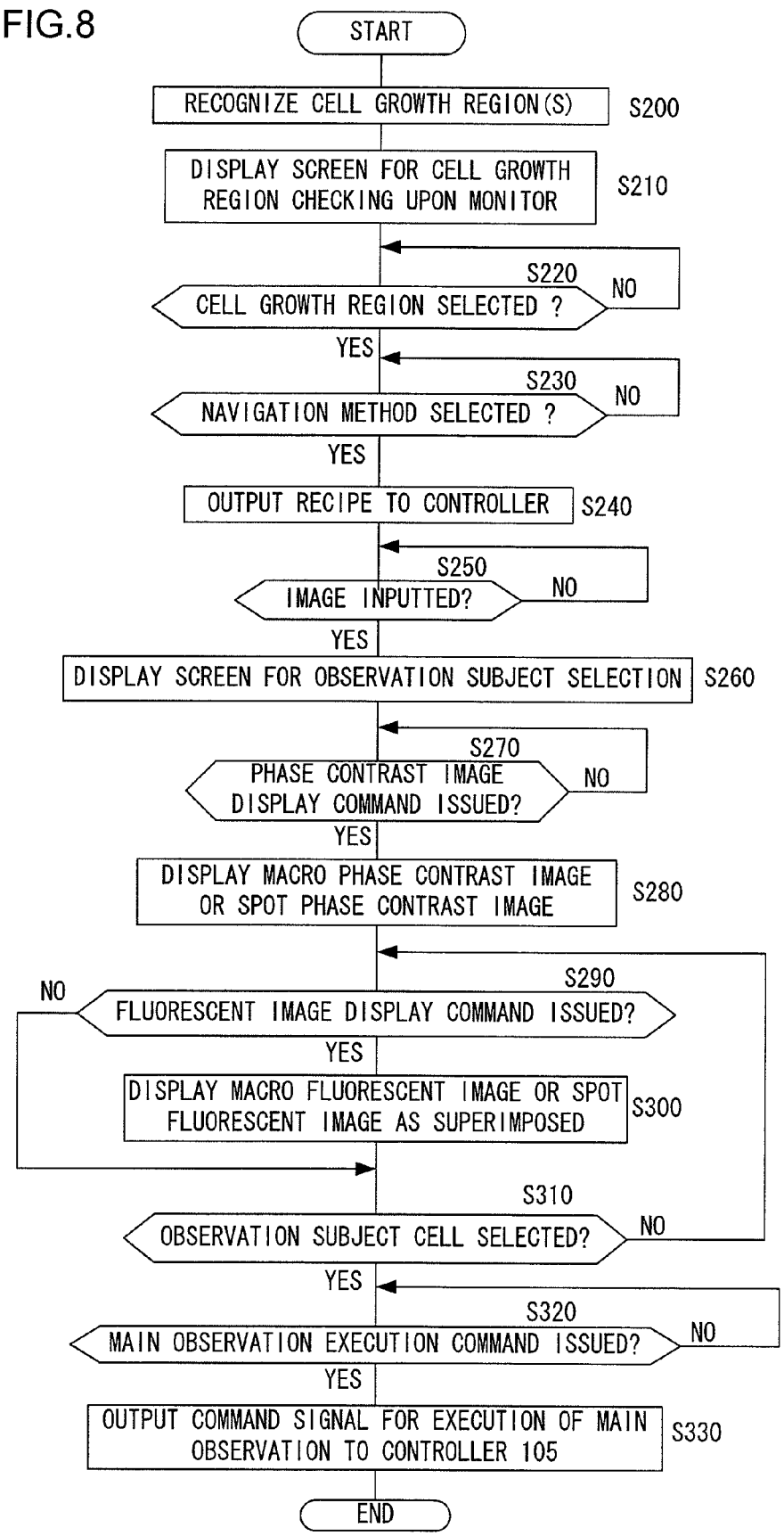
FIG. 8 is a flow chart showing the flow of processing of a PC 109.

FIG. 8 is a flow chart showing the flow of processing of the PC 109. The processing shown in FIG. 8 is executed by the CPU incorporated in the PC 109 according to a program that is started when the above described macro images are inputted from the controller 105.

In a step S200, the macro images that have been input are analyzed by using a per se known for of image analysis such as texture analysis or the like, the cell growth region(s) in the macro images in which cells are growing are recognized, and then the flow of control proceeds to a step S210. In this step S210, the screen for growth region checking described above in FIG. 2 is displayed upon the monitor 110, and a macro image in which the cell growth region(s) are marked out is displayed in the macro image display region 2a. Then the flow of control proceeds to a step S220.

In this step S220 a decision is made as to whether or not, by actuation of the shift button 2b by the user, a cell growth region or regions that are to be the subject of execution of navigation have been selected. If it is decided that a cell growth region has been selected, then the flow of control proceeds to a step S230, in which a decision is made as to whether either the tiling mode or the random mode has been selected as the method for executing navigation to the selected cell growth region(s). If it is decided that some navigation method has been selected, then the flow of control proceeds to a step S240.

In this step S240, a recipe is created in which are stored navigation range information or navigation spot information corresponding to the navigation method that has been selected, information specifying the navigation method, and information specifying the photographic conditions, and this recipe is then outputted to the controller 105. Then the flow of control proceeds to a step S250.

In this step S250 a decision is made as to whether or not images corresponding to the navigation method—i.e., in the case of the tiling mode, a macro phase contrast image and one or more macro fluorescent images, and in the case of the random mode, one or more spot phase contrast images and spot fluorescent images—have been inputted from the controller 105. If it has been decided that such images have been inputted, then the flow of control proceeds to a step S260. In this step S260 the screen for observation subject selection shown in FIG. 5 is displayed upon the monitor 110, and then the flow of control proceeds to a step S270.

In this step S270 a decision is made as to whether or not, by the phase contrast image display button 5a being selected by the user upon the screen for observation subject selection, a command has been issued for display of a macro phase contrast image or of a spot phase contrast image. If it has been decided that a command for display of a macro phase contrast image or of a spot phase contrast image has been issued, then the flow of control proceeds to a step S280, in which, according to the navigation method, a macro phase contrast image or a spot phase contrast image is displayed within the image display region 5d upon the screen for observation subject selection. Then the flow of control proceeds to a step S290.

In this step S290, a decision is made as to whether or not display of a macro fluorescent image or of a spot fluorescent image has been commanded by the user selecting, upon the screen for observation subject selection, a fluorescent image display button that corresponds to some type of fluorescent filter. If it is decided than no command for display of a macro fluorescent image or of a spot fluorescent image has been issued, then the flow of control is transferred to a step S310 that will be described hereinafter. By contrast, if it is decided that a command for display of a macro fluorescent image or of a spot fluorescent image has been issued, then the flow of control proceeds to a step S300, in which the fluorescent image for the fluorescent filter that has been commanded is displayed as superimposed upon the phase contrast image that is being displayed within the image display region 5d. Then the flow of control proceeds to the step S310.

In this step S310, a decision is made as to whether or not a cell has been selected by the user as the subject for observation. If it is decided that no cell is selected as the observation subject, then the flow of control returns to the step S290 and the above processing is repeated. By contrast, if it is decided that a cell has been selected as the observation subject, then the flow of control proceeds to a step S320. In this step S320, a decision is made as to whether or not a command for execution of the main observation has been issued by the user. If it is decided that such a command for execution of the main observation has been issued, then the flow of control proceeds to a step S330, in which a command signal for execution of the main observation is outputted to the controller 105, and then this processing terminates.

According to this embodiment as explained above, the following beneficial operational effects may be obtained.

(1) It is arranged to analyze the macro image by a per se known technique of image analysis such as texture analysis or the like, to recognize the cell growth regions within the macro image, and to display the cell growth regions that have been recognized explicitly upon the macro image. By doing this, the user is able visually to check whether or not cell growth regions are present, and at what positions they are within the observable range. Moreover since, after automatic recognition of the cell growth regions has been performed, these regions are displayed, accordingly it is possible reliably to ascertain just which regions are the cell growth regions.

(2) It is arranged for it to be possible to select at least one from among the cell growth regions that are shown upon the macro image as the subject for execution of navigation, and for navigation to be executed to the cell growth region or regions that have been selected by the user. Due to this, it is possible to limit the subjects for execution of navigation to only those regions in which the cells are growing, so that it is possible to reduce the burden of the processing.

(3) For each small region within the navigation range, it is arranged to irradiate excitation light upon the cells, and to perform photography of a fluorescent image, for only the time period that is required for photography of that image, and to provide to the user a macro fluorescent image produced by tiling these fluorescent images that have been photographed for each of these small regions. Due to this, it is possible to reduce the damage caused at this preparatory stage to the cells due to photobleaching and phototoxicity to the minimum possible level. Moreover, the user is able to select upon the macro phase contrast image the cell or cells that are to be the subject for observation while taking his time, without any concern for any bad influence that might be exerted upon the cells due to continuation of irradiation of the excitation light.

(4) For each small region within the navigation range, it is arranged to irradiate transmitted light upon the cells, and to perform photography of a phase contrast image, for only the time period that is required for photography of that phase contrast image, and to provide to the user a macro phase contrast image produced by tiling these phase contrast images that have been photographed for each of these small regions. Due to this, even when observing cells which are subject to the possibility of suffering a bad influence, not only due to the influence of irradiation of the excitation light, but also due to the influence of irradiation of this transmitted light, it is still possible to perform photography of a phase contrast image while suppressing the bad influence exerted upon the cells due to this irradiation of the transmitted light to the minimum possible level. In other words, since it is arranged to perform specification of the observation subject for the main observation upon the image that has been photographed, accordingly it is possible to reduce the bad influence upon the cells due to the irradiation of the excitation light or of the transmission light to the minimum possible level, since the excitation light and the transmitted light are irradiated only when acquiring (i.e. photographing) the image.

(5) It is arranged for the objective lens 103 to perform fluorescent observation while changing over the plurality of fluorescent filters, and for the camera 104 to photograph a fluorescent image for each of these fluorescent filters. Due to this, even when multiple dyeing has been performed by dyeing with a plurality of fluorescent reagents, it is still possible to perform photography of one fluorescent image for each fluorescent color.

(6) If the tiling mode has been selected as the navigation method, then it is arranged to build up single macro images that have been photographed over the navigation range by tiling together the phase contrast images and the fluorescent images over the navigation range that have been individually photographed for each small region while executing navigation, and to display these tiled images upon the monitor 110. By doing this, it is possible for the user to select the cell or cells that are to become the subject for observation from the entire navigation range.

(7) If the random mode has been selected as the navigation method, then it is arranged to display the phase contrast image and the fluorescent image(s) for each navigation spot upon the monitor 110. By doing this, it is possible for the user to obtain a phase contrast image and fluorescent image(s) for each small region centered around each of the navigation spots that have been automatically selected, even without himself designating the navigation spot each time. Thus the convenience of use from the point of view of the user is enhanced.

(8) It is arranged for the user to be able to select cells, within the image display region 5d upon the screen for observation subject selection that is displayed upon the monitor 110, by displaying the phase contrast image and a fluorescent image for each of the fluorescent filters, as mutually superimposed. By doing this, it is possible for the user to perform selection of the cell or cells that are to become the subject for observation while checking, not only the shapes of the cells, but also their state of fluorescence due to the fluorescent reagent.

Variant Embodiments

It should be understood that the cell observing apparatus of the embodiment described above may also be varied as described below.

(1) In the embodiment described above, it is arranged for it to be possible to display at least one of the plurality of fluorescent images within the image display region 5d upon the screen for observation subject selection that is displayed upon the monitor 110, as superimposed over the phase contrast image, and thereby to select a cell or cells. However this is not to be considered as being limitative; it would also be acceptable to arrange to superimpose two or more of the plurality of fluorescent images. Furthermore, it would also be acceptable to arranged for it to be possible to magnify the macro image displayed within the image display region 5d. By doing this, it would become possible for the user to magnify the macro image further, and thereby to select the cell or cells that are to become the subject of observation in a simple and easy manner.

(2) In the embodiment described above, an example was explained in which the phase contrast images and the fluorescent images for each of the small regions, that have been obtained by executing navigation processing over the navigation range, are combined together so as to build up the macro phase contrast image and the macro fluorescent image or images. However, it would also be acceptable to arrange to perform photography of one only of a phase contrast image and a fluorescent image. In this case, the user would select the cell(s) to be the subject of the main observation while checking either the macro phase contrast image or the macro fluorescent image upon the screen for observation subject selection.

(3) In the embodiment described above, an example was explained in which the user selected the cell(s) to be the subject of observation upon the screen for growth region checking shown in FIG. 2; but the layout of the screen for growth region checking is not limited to the one shown in FIG. 2.

(4) In the embodiment described above, an example was explained in which the user selected the cell(s) to be the subject for observation upon the screen for observation subject selection shown in FIG. 5, but the layout of the screen for observation subject selection is not limited to the one shown in FIG. 5 either.

(5) In the embodiment described above, an example was explained in which the controller 105 executed the processing shown in FIG. 7, and the PC 109 executed the processing shown in FIG. 8. However, it would also be acceptable for all of the processing shown in FIGS. 7 and 8 to be performed by either the controller 105 or the PC 109.

(6) In the embodiment described above an example was explained in which, for the main observation, time lapse processing was executed upon the cell(s) that are the subject for observation, but the present invention can also be applied to a case in which a cell or cells are selected as a preparatory step when an observation is to be performed by some other observation method, or when a test is to be performed.

(7) In the embodiment described above, a case was explained in which cells were taken as the subject for observation, but the present invention can also be applied to some other subject for observation, for example a mineral or the like, that can be observed by irradiation of light, and moreover for which there is a possibility of a bad influence being exerted due to such irradiation of light.

(8) In the embodiment described above, an example was explained in which the macro images were acquired by using an objective lens of low magnification of 4×, that can observe a wide field of view. However, it would also be acceptable for the magnification that is used when acquiring the macro images to be from around 1× to around 200×. Desirably, however, this magnification should be from about 2× to around 100×, and even more desirably it should be from about 2× to around 50×. One of the objectives of acquiring the macro images is the objective of providing a function of mapping from the macro images that are acquired, in other words of providing a function for searching the observation region. Accordingly, if an image is acquired at quite high magnification, for example at 500×, then it becomes impossible to obtain an image of anything other than a narrow region within the entire area of the test specimen for observation; in other words, it becomes impossible to generate a map of anything except a narrow range, so that thereafter the search region becomes restricted to this detailed observation region. Moreover, it would also be acceptable to arrange to acquire the macro images for the test specimen that is to be observed at a magnification of 1×. Even further it would also be acceptable, if for example the test specimen for observation is contained within a Petri dish, to acquire an image in which the entire Petri dish is displayed upon the display device. As the magnification in this case, it would even be acceptable to arrange for this image to be acquired at a magnification that is lower than 1×, for example 0.5×.

(9) It should be understood that, when acquiring a macro image at a magnification such as that described above, it is desirable for the magnification when photographing the cells in the observation object region to be a magnification that is higher than the magnification when generating the macro images. This magnification when photographing the cells in the observation object region varies according to the form and the type of the test specimen under observation, and according to the objective of observation and the like. Accordingly, while for example the macro image may be acquired at a magnification of 2×, it would be acceptable to arrange to use a magnification of 3× when acquiring the images of the cells in the observation object region. However, it would also be acceptable for the magnification when generating the macro images and the magnification when acquiring the images of the cells in the observation object region to be at a one-to-one ratio. If for example the macro image is acquired at a ratio of 200×, then it would be acceptable to arrange to acquire the images of the cells in the observation object region at a magnification of 200× as well, if, according to decision by the user, this is a magnification that will be satisfactory as a magnification while acquiring the images of the cells in the observation object region.

(10) In the embodiment described above an example was explained in which, using an objective lens of a low magnification such as 4× or the like that can perform observation over a wide field of view, phase contrast images of an entire region within the observable region are photographed while shifting the objective lens, and a single macro image is built up by tiling together the plurality of images that have been photographed. However this is not to be considered as being limitative; it would also be acceptable to arrange to build up the macro image by tiling together images of the entire region within the observable region that have been photographed by some other contrast enhancement method than fluorescence, such as a differential interference contrast method or the like.

(11) In the embodiment described above it was arranged, when the random mode was selected as the navigation method, to invite the user to input the number of spots that are to be set as navigation spots, and, according thereto, to select spots to the number that has been inputted by the user at random as navigation spots. However, it would also be acceptable to use a number of navigation spots that is fixed at a constant value set in advance by the user, or to display an initial value that is set in advance and to make it possible for the user then to change the number of navigation spots as desired.

(12) In the embodiment described above, an example was explained in which, in the building up of the macro image and the macro phase contrast images, building up of images that have been observed by phase contrast is performed. However the present invention is not limited to phase contrast observation; it would also be acceptable for these images to be images that have been observed by bright field observation, differential interference contrast observation, polarized light observation, dark-field observation, or the like. In this type of case as well, the excitation light that is outputted from the excitation light source unit 108 is intercepted by the shutter 107, and the respective observations are performed by irradiating illumination light as is respectively suitable.

Figure 9:
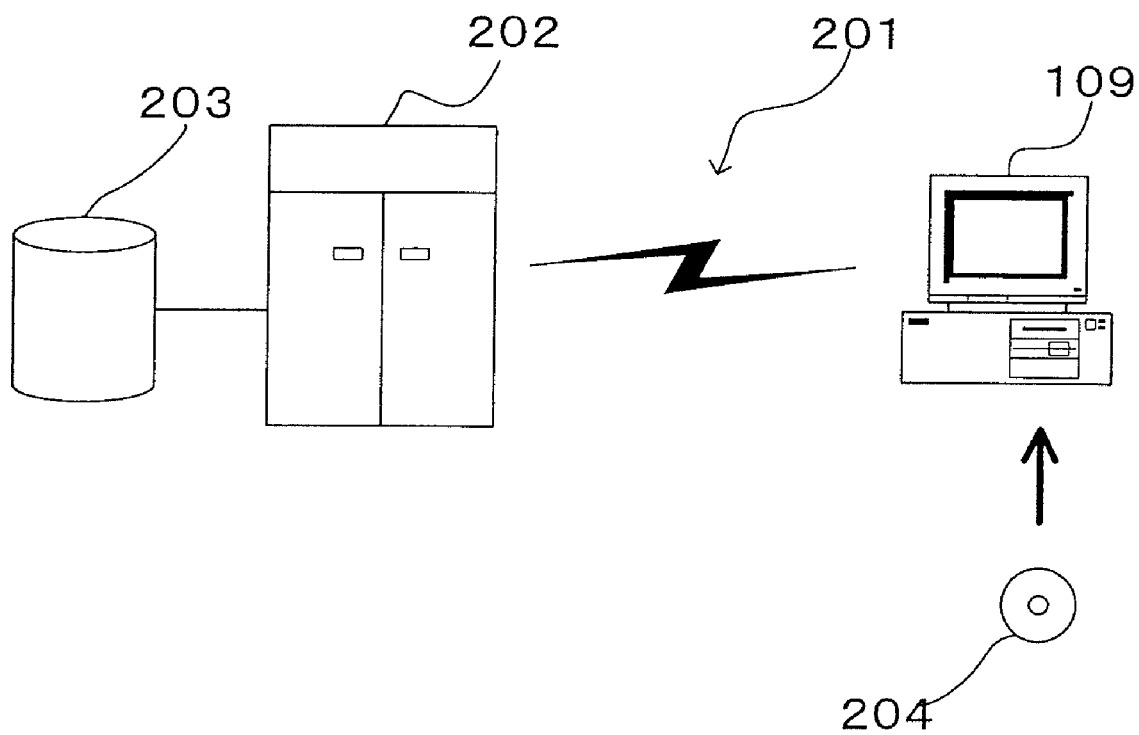
FIG. 9 is a figure showing a situation in which a program is supplied to the PC 109.

(13) The controller 105 of the embodiment described above may be replaced by a personal computer or the like. If the controller 105 is replaced by a computer in this manner, then the processing program described above for the controller 105 may be supplied via a recording medium such as a CD-ROM or the like, or via a data signal such as the internet or the like. Moreover, the processing program described above for the PC 109 may also be supplied via a recording medium such as a CD-ROM or the like, or via a data signal such as the internet or the like. FIG. 9 is a figure showing methods according to which, by way of example, such a program may be supplied to the PC 109. The PC 109 receives supply of the program via a CD-ROM 204. Furthermore, the PC 109 may be endowed with the function of communication to a communication circuit 201. A computer 202 is a server computer that supplies the program described above, and that stores the program upon a recording medium such as a hard disk 203 or the like. The communication circuit 201 is a communication circuit such as the internet or the like, or a dedicated communication circuit or the like. The computer 202 reads out the program using its hard disk 203, and transmits the program to the PC 109 using the communication circuit 201. In other words, the program is carried as a data signal upon a carrier wave, and is thereby transmitted via the communication circuit 401. By doing this, the program may be supplied as a computer program product in various different modes that can be read in by a computer, such as a recording medium or a carrier wave or the like.

It should be understood that the present invention is in no way limited by the embodiments described above, provided that the characteristic functions of the present invention are not lost.

What is claimed is:

1. An observing apparatus, comprising:
   a photographic unit that photographs cells based upon a macro image of an interior of a cell culture vessel in which the cells are put;
   an illuminating unit that irradiates light only during photography by the photographic unit;
   an output unit that outputs a fluorescent image photographed by the photographic unit while irradiating light only during photography by the illuminating unit;
   a recognition section that recognizes at least one observation region, within the macro image, in which cells are present;
   an objective lens;
   a selection unit that selects a tiling mode or a random mode; and
   a controller that, when either the tiling mode or the random mode is selected, points the objective lens at an observation region in which the recognition unit has recognized that cells are present.

2. An observing apparatus according to claim 1, further comprising:
   an excitation light source that, during fluorescent observation, irradiates excitation light that excites a fluorescent reagent added to a specimen; and
   a shutter that can either intercept or allow irradiation of light from the excitation light source upon the specimen, wherein:
   the controller controls the shutter so as to intercept the irradiation of light from the excitation light source upon the specimen, when the objective lens is facing to an observation position.

3. An observing apparatus according to claim 2, wherein:
   the controller acquires a macro image of the observation region by, after having intercepted the excitation light with the shutter, performing observation by phase contrast observation, bright field observation, differential interference contrast observation, polarized light observation, or dark-field observation.

4. An observing apparatus according to claim 3, wherein:
   after the macro image of the observation region has been acquired, the controller opens the shutter, irradiates excitation light from the excitation light source upon the specimen, and acquires a fluorescent image of the observation region.

5. An observing apparatus according to claim 4, further comprising:
   a storage unit that stores the fluorescent image that has been acquired, wherein:
   the controller superimposes the fluorescent image of the observation region and the macro image of the observation region that are stored in the storage unit.

* * * * *